United States Patent
Rice

(10) Patent No.: US 10,851,416 B2
(45) Date of Patent: Dec. 1, 2020

(54) PREDICTIVE NEURODIAGNOSTIC METHODS

(71) Applicant: LIKEMINDS, INC., Auburndale, MA (US)

(72) Inventor: Kenneth L. Rice, Wellesley, MA (US)

(73) Assignee: LIKEMINDS, INC., Boston, MA (US)

( * ) Notice: Subject to any disclaimer, the term of this patent is extended or adjusted under 35 U.S.C. 154(b) by 226 days.

(21) Appl. No.: 15/321,318

(22) PCT Filed: Jun. 24, 2015

(86) PCT No.: PCT/US2015/037340
§ 371 (c)(1),
(2) Date: Dec. 22, 2016

(87) PCT Pub. No.: WO2015/200434
PCT Pub. Date: Dec. 30, 2015

(65) Prior Publication Data
US 2017/0198349 A1    Jul. 13, 2017

Related U.S. Application Data

(60) Provisional application No. 62/016,309, filed on Jun. 24, 2014, provisional application No. 62/016,315, (Continued)

(51) Int. Cl.
*G16H 50/20* (2018.01)
*C12Q 1/6883* (2018.01)
(Continued)

(52) U.S. Cl.
CPC ....... *C12Q 1/6883* (2013.01); *G01N 33/6896* (2013.01); *G06T 7/0012* (2013.01);
(Continued)

(58) Field of Classification Search
None
See application file for complete search history.

(56) References Cited

U.S. PATENT DOCUMENTS 7,401,028 B2   7/2008   Deakter
8,280,750 B2   10/2012  Krishnan et al.
(Continued)

FOREIGN PATENT DOCUMENTS

WO   2008061209 A2    5/2008
WO   WO 2011/159592 A1   12/2011
(Continued)

OTHER PUBLICATIONS

PCT International Search Report for PCT International Application No. PCT/US2015/037340; dated Dec. 4, 2015; (5 pages).
(Continued)

*Primary Examiner* — Ankit D Tejani
(74) *Attorney, Agent, or Firm* — Ann-Louise Kerner

(57) ABSTRACT

Disclosed are methods of predicting the risk of developing a neurological disorder in a mammalian subject and methods of use of this profile for providing neuroanalytical services for an end user. Also disclosed is a system comprising a processor and a memory having a neurodiagnostic algorithm and plurality of data sets, the processor being capable of reading the data sets, executing the neurodiagnostic algorithm, and deriving a risk profile therefrom.

15 Claims, 1 Drawing Sheet

Related U.S. Application Data filed on Jun. 24, 2014, provisional application No. 62/016,302, filed on Jun. 24, 2014, provisional application No. 62/094,214, filed on Dec. 19, 2014, provisional application No. 62/094,219, filed on Dec. 19, 2014, provisional application No. 62/094,223, filed on Dec. 19, 2014.

(51) Int. Cl.
*G01N 33/68* (2006.01)
*G06T 7/00* (2017.01)
*G16H 50/30* (2018.01)
*G16H 10/60* (2018.01)

(52) U.S. Cl.
CPC ....... *G16H 50/20* (2018.01); *C12Q 2600/118* (2013.01); *C12Q 2600/156* (2013.01); *C12Q 2600/158* (2013.01); *C12Q 2600/178* (2013.01); *G01N 2800/50* (2013.01); *G16H 10/60* (2018.01); *G16H 50/30* (2018.01); *Y02A 90/10* (2018.01)

(56) References Cited

U.S. PATENT DOCUMENTS

| | | | |
|---|---|---|---|
| 8,566,123 | B2 | 10/2013 | Mansour et al. |
| 8,615,413 | B2 | 12/2013 | McKee et al. |
| 8,655,817 | B2 | 2/2014 | Hasey et al. |
| 2005/0283054 | A1 | 12/2005 | Reoicman et al. |
| 2009/0099474 | A1* | 4/2009 | Pineda .............. A61B 5/121 |
| | | | 600/545 |
| 2010/0016743 | A1 | 1/2010 | Syed et al. |
| 2011/0213278 | A1* | 9/2011 | Horak ............... A61B 5/4082 |
| | | | 600/595 |
| 2012/0071779 | A1* | 3/2012 | Sarkela ............. A61B 5/048 |
| | | | 600/544 |
| 2012/0238936 | A1* | 9/2012 | Hyde ............... A61B 5/14507 |
| | | | 604/8 |
| 2012/0284045 | A1 | 11/2012 | Hicks et al. |
| 2013/0124224 | A1 | 5/2013 | Srinivasan et al. |
| 2013/0173282 | A1 | 7/2013 | Tee |
| 2014/0022255 | A1 | 1/2014 | Barbouche et al. |
| 2014/0052464 | A1 | 2/2014 | Ray |
| 2014/0162933 | A1 | 6/2014 | Hatchwell et al. |

FOREIGN PATENT DOCUMENTS

| | | |
|---|---|---|
| WO | WO 2012/012714 A2 | 1/2012 |
| WO | 2013134403 A1 | 9/2013 |
| WO | 2014085830 A2 | 6/2014 |

OTHER PUBLICATIONS

PCT Written Opinion for PCT International Application No. PCT/US2015/034340; dated Dec. 4, 2015; (9 pages).

Asphahani et al. (2007) "Cellular impedance biosensors for drug screening and toxin detection," Analyst 132(9):835-841.

Benson, D. (1993) "The history of behavioral neurology," Neurol. Clin. 11(1): 1-8.

Maller, J. et al. (2006) "Common variation in three genes, including a noncoding variant in CFH, strongly influences risk of age-related macular degeneration," Nat Genet. 38:1055-1059.

The Fourth National Report on Human Exposure to Environ. Chem. (2009) CDCP.

Wang, L. et al. (2009) "Simple, Rapid, Sensitive, and Versatile SWNT-Paper Sensor for Environmental Toxin Detection Competitive with ELISA," Nano Lett. 9(12):4147-4152.

\* cited by examiner

GLOBAL CNS Dx Solution
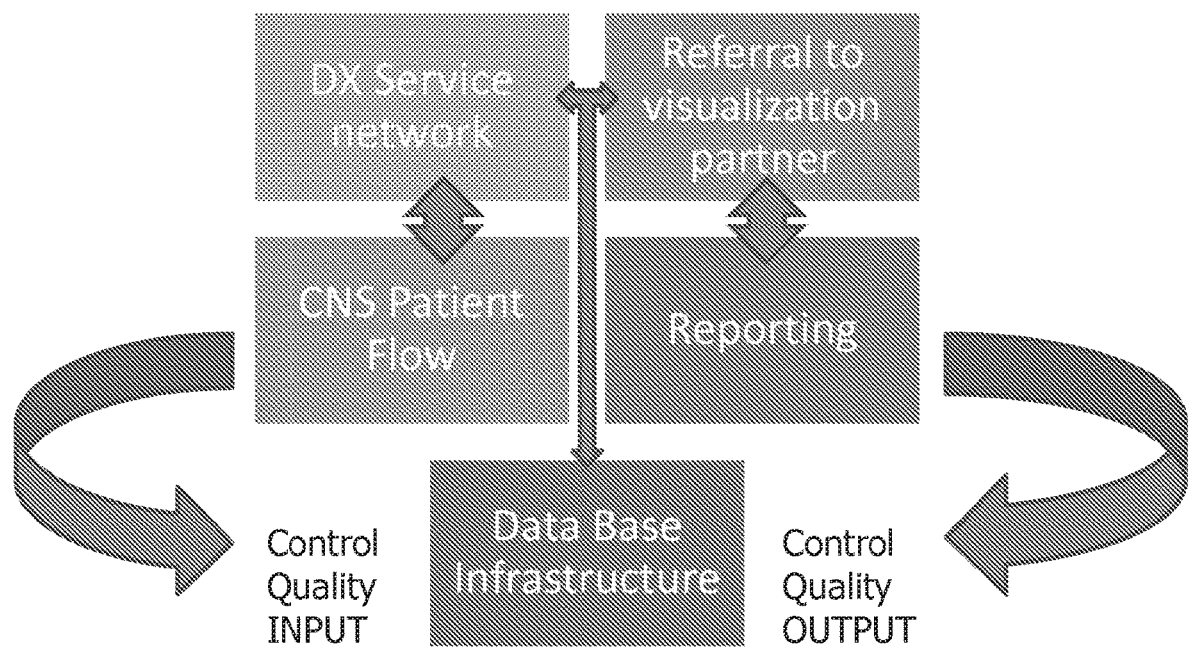

PREDICTIVE NEURODIAGNOSTIC METHODS

CROSS REFERENCE TO RELATED APPLICATIONS

This application is a U.S. National Stage application based on PCT International Application No. PCT/US2015/037340 filed Jun. 24, 2015, which claims the benefit of U.S. Provisional Patent Application Ser. No. 62/016,302 entitled "Predictive Neurodiagnostic Methods," which was filed Jun. 24, 2014, U.S. Provisional Patent Application Ser. No. 62/016,309 entitled "Neuroanalytical Services," which was filed Jun. 24, 2014, U.S. Provisional Patent Application Ser. No. 62/016,315 entitled "Neurodiagnostic-Analysis System," filed on Jun. 24, 2014, U.S. Provisional Patent Application Ser. No. 62/094,214 entitled "Predictive Neurodiagnostic Methods," which was filed Dec. 19, 2014, U.S. Provisional Patent Application Ser. No. 62/094,219 entitled "Neuroanalytical Services," which was filed Dec. 19, 2014, and U.S. Provisional Patent Application Ser. No. 62/094,223 entitled "Neurodiagnostic Analysis System," filed on Dec. 19, 2014. The entirety of the aforementioned applications are herein incorporated by reference.

FIELD OF THE INVENTION

The present disclosure relates to systems and methods for evaluating neurological disorders, and to databases and computational systems for predicting disease and treatment outcomes.

BACKGROUND

According to multiple patent advocacy groups around the globe, the prevalence of many neurological disorders, including those affecting the aging population in the developed countries of the world, is estimated at over 20 million people today and is expected to quadruple in the next twenty years. Research and development of treatments by pharmaceutical and biotech companies for these disorders has lagged behind disease prognosis. Clinical trials for the few new therapeutic drugs require huge financial expenditures by these companies, and often they fail because they are looking for drugs that are for "one size fits all" patients.

Furthermore, the presently available therapeutics may only be temporarily or mildly efficacious, as the patient group for which the drug was developed was different than the present patient in need of treatment. In some cases, presently available therapeutics are not efficacious at all because the damage done to the CNS before diagnosis of the disorder and subsequent treatment may be irreversible.

Providing treatment to a patient at an earlier stage of the disease, or better yet, before the disease presents itself in an asymptomatic patient and causes irreparable damage to the nervous system of the patient, would be beneficial.

Data on patients with neurological disorder do exist, as it is collected by hospitals, universities, disease foundations, and pharmaceutical companies undertaking preclinical and clinical trials. In addition, the incidence of patients self-initiating testing such as DNA and biomarker analysis is increasing. However, all of this existing data is not centrally located, in many cases is in too small a sample size and is thus not statistically and/or clinically relevant, and often is obtained with selection biases and over a limited time frame. Thus, comprehensive data on patient populations does not exist, and this data is needed to design targeted drugs and diagnostics against specific diseases and populations of patients.

Thus, what is needed are comprehensive, controlled databases of neurological information on single patients and on worldwide populations of patients and controls. What is also needed for drug and diagnostic development are global databases of neurological information from specific, qualified clinical trial populations.

SUMMARY

In one aspect, the disclosure provides a method of predicting the risk of developing a neurological disorder in a first mammalian subject. The subject may be asymptomatic or symptomatic. The method comprises the steps of: screening for the presence of one or more biomarkers; performing diagnostic imaging of the subject; performing behavioral tests indicative of the neurological disorder; measuring the subject's exposure to an environmental factor; measuring/identifying a physical characteristic of the subject; determining the presence of the neurological disorder in a family member of the first subject; combining the results from the steps above; and comparing the combined results with combined results obtained from a second mammalian subject diagnosed with the neurological disorder, a high correlation between the combined results from the second subject and the combined results obtained from the first subject being indicative of a heightened risk of the first subject developing the neurological disorder.

As used herein, a "high" or "heightened correlation" refers to a correlation coefficient of at least 0.7. Correlations can range from 0 (no correlation) to 1 (maximum correlation). When two variables have a correlation of 1, it means that the value of one variable can be predicted by the value of the other variable. Likewise, a low correlation means the 2 variable values have little to do with each other.

In some embodiments, the screening step comprises screening for a biomarker which is a nucleic acid, polypeptide, prion, virus, brain plaque, CNS plaque, fibril, intranuclear neuronal inclusions, and/or brain structure abnormality. In certain embodiments, the biomarker is a nucleic acid such as a gene, or coding portion thereof, a SNP, an mRNA, a miRNA, a pri-miRNA, or a prepri-miRNA. In particular embodiments, nucleic acid biomarker is over-expressed miR-196a, miR-29a, or miR-330. In other particular embodiments, the nucleic acid biomarker is under-expressed miR-133b, miR-205, miR-34b/c, miR-9, miR-9*, or miR-132. In different embodiments, the nucleic acid biomarker is a mutated Cu/Zn superoxide dismutase 1 (SOD1) gene, an unstable microsatellite repeat (insertion mutation) in a gene, a mutated HTT gene, androgen receptor gene (on the X chromosome), ATXN1, ATXN2, ATXN3, ATXN7, TBP, CACNA1A, C9orf72 (on chromosome 9), FMR1 (on the X-chromosome), AFF2 (on the X-chromosome), FMR2 (on the X-chromosome), FXN or X25, (frataxin-reduced expression), DMPK, OSCA or SCA8, PPP2R2B or SCA12, α-synuclein, glucocerebrosidase (GBA), ABHD12, SNCA, or LRRK2. or a leucine-rich repeat kinase 2 (LRRK-2) gene. In yet other embodiments, the biomarker is a polypeptide which is a surface marker, tau protein, beta amyloid, polyglutamate (peptide), alpha-synuclein, non-Abeta component (NAC), polyQ expansion, TDP-43 protein aggregate, FUS protein aggregate, or mutant Huntingtin aggregate. In some embodiments, the biomarker an aberrant structure such as is a Lewy body fibril, neurofibrillary tangle, or alpha-synuclein fibril, or is an amyloid plaque or a senile plaque. In still other embodiments, the biomarker is a virus such as Herpes simplex virus-1 (HSV-1 type HHV-1), roseolovirus (type HHV-6), Epstein Barr virus (EBV type HHV-4), Varicella zoster virus (VZV type HHV3), H1N1 Influenza a viruses, HIV, and/or HTLV-II, or a particle of a virus.

In some embodiments, the screening step is performed by obtaining a sample of a body fluid or tissue and screening for the biomarker in the sample. In certain embodiments, the sample is obtained from the subject's blood, cerebral spinal fluid, serum, lymph, saliva, lacrimal secretion, sweat, mucous, vaginal secretion, lymph, urine, or seminal fluid.

In certain embodiments, the diagnostic imaging step of the method performed obtaining an x-ray, a computerized axial tomographic (CAT) scan, magnetic resonance imaging (MRI) scan, functional MRI (fMRI) for blood-oxygen-level-dependent (BOLD) imaging, single photon emission computed tomography (SPECT) perfusion image, computed tomography (CT) scan, proton MR spectroscopy scan, positron emission tomographic (PET) scan, and/or [F-18] fluoro-2-deoxy-D-glucose-positron emission tomographic (18F-FDG PET) scan, and/or ultrasound scan. In certain embodiments, these scans employ radio-labeled imaging reagents which target specific receptors on neurons or proteins in the brain. In specific embodiments, the imaging reagent is DaTScan, Amyvid, or similar reagents.

In some embodiments, the behavioral test performed measures sensory abilities, motor functions, body weight, body temperature, and/or pain threshold, learning abilities, memory, and symptoms of anxiety, depression, schizophrenia, and/or drug addiction.

In certain embodiments, the behavioral test performed measures acoustic startle, eye blink, pupil constriction, visual cliff, auditory threshold, and/or olfactory acuity.

In some embodiments, wherein the subject's exposure to pesticides, herbicides, fungicides, solvents, other toxic chemicals, tobacco smoke, heavy metals, electromagnetic fields, ultraviolet radiation, and/or diet (malnutrition, vitamin deficiency), and/or alcohol consumption is measured. In particular embodiments, the subject's exposure to MPTP (1-methyl-4-phenyl-1,2,3,6-tetrahydro-pyridine), rotenone, paraquat, maneb, Agent orange, manganese, lead, iron, methylmercury, copper, zinc, selenium, polychlorinated biphenyls, and/or a reactive oxygen species (ROS) is measured. In certain embodiments, exposure of the subject to the environmental factor causes apoptosis, oxidative stress, perturbed calcium homeostasis (loss of intracellular $Ca^{+2}$), excitotoxicity, mitochondrial dysfunction, and/or activation of caspases.

In other embodiments, the physical factor measured is the age, gender, ethnicity, heart rate, REM, electrical signals from the heart or brain, and/or the presence of genetic polymorphisms, endocrine conditions, oxidative stress, inflammation, stroke, traumatic brain injury, hypertension, diabetes, head/CNS trauma, depression, infection, cancer, vitamin deficiency, and/or immune and/or metabolic condition of the subject.

The present method is predictive of a neurological disorder such as neurodegenerative, neurotrauma, or neuropsychology disorders.

In some embodiments, the neurological disorder is a neurodegenerative disorder such as a polyglutamine (PolyQ) disease or a non-polyglutamine disease. In certain embodiments, the polyglutamine disease is Spinocerebellar ataxia type 1 (SCA1), SCA2 (Spinocerebellar ataxia Type 2), SCA3 (Spinocerebellar ataxia Type 3 or Machado-Joseph disease), SCA6 (Spinocerebellar ataxia Type 6), SCA7 (Spinocerebellar ataxia Type 7), SCA17 (Spinocerebellar ataxia Type 17), DRPLA (Dentatorubropallidoluysian atrophy), HD (Huntington's disease), SBMA (Spinobulbar muscular atrophy or Kennedy disease), dentatorubral atrophy, or pallidoluysian atrophy. In other embodiments, the non-polyglutamine disease is FRAXA (Fragile X syndrome), FXTAS (Fragile X-associated tremor/ataxia syndrome), FRAXE (Fragile XE mental retardation), FRDA (Friedreich's ataxia), DM (Myotonic dystrophy), SCA8 (Spinocerebellar ataxia Type 8), or SCA12 (Spinocerebellar ataxia Type 12.

In other embodiments, the neurological disorder is a neurotrauma disorder resulting from a traumatic brain injury or concussion, or from a stroke.

In yet other embodiments, the neurological disorder is a neuropsychology disorder such as autism, ADHD, anxiety, depression, bipolar disorder, dyslexia, epilepsy, obsessive compulsive disorder, schizophrenia, or social phobia. It yet other embodiments, the neuropsychology disorder is Arachnoid cysts, Arachnoiditis, Asperger's Syndrome, Ataxia Telangiectasia, Arteriovenous Malformations, Attention Deficit/Hyperactivity Disorder, Autism Barth Syndrome, Batten Disease, Behcet's Disease, Bell's Palsy Bernhardt-Roth Syndrome, Binswanger's Disease, Blepharospasm Bloch-Sulzberger Syndrome, Brown-Sequard Syndrome, CADASIL Canavan Disease, Capgras Syndrome, Causalgia Central Cord Syndrome, Central Pain Syndrome, Central Pontine Myelinolysis, Cerebellar Hypoplasia, Cerebral Anoxia/Hypoxia, Cerebral Arteriosclerosis, Cerebral Cavernous Malformations, Cerebral Palsy, Cerebro-Oculo-Facio-Skeletal Syndrome, Charcot-Marie-Tooth Disease, Chiari Malformations, Childhood Anxiety Disorders, Childhood Disintegrative Disorder, Childhood Mood Disorders, Cholesteryl-Ester Storage Disease, Chronic Inflammatory Demyelinating Polyneuropathy, Chronic Pain Syndrome, Chung-Strauss Syndrome, Cluster Headaches Coffin-Lowry Syndrome, Colpocephaly Coma & Persisting Vegetative State Conduct Disorder, Oppositional Defiant Disorder, Congenital Myasthenia Congenital Myopathy, Corticobasal Degeneration, Craniosynostosis, Creutzfeld-Jakob Disease, Cushing's Disease, CVAs, Cytomegalovirus Dandy-Walker Syndrome, Dawson Disease, De Morsier's Syndrome, Dejerne-Klumpke Palsy Delirium, Dementia Pugilistica, Dermatomyositis, Devic's Disease, Diabetic Neuropathy, Disconnect Syndromes, Disorders of Written Language, Down Syndrome, Dravet Syndrome, Dysautonomia, Dyssynergia, Cerebellaris Myoclonica Dystonias, Empty Sella Syndrome, Encephalitis, Encephalopathy, Encephalo-celes, Epilepsy, Erb-Duchenne Palsy, Fabry Disease, Fahr's Syndrome, Familial Periodic Paralyses, Familial Spastic Paraplegia, Farber's Disease, Fatal Familial Insomnia, Febrile Seizures, Fibromuscular Dysplasia, Fibromyalgia, Fragile X Syndrome, Friedeich's Ataxia, Frontotemporal Dementia, Gaucher Disease, Gerstmann-Straussler-Scheinker Disease, Gerstmann Syndrome, Glossopharyngeal neuralgia, Guillain-Barre, Hallervorden-Spatz Disease, Hemicrania, Continua Hemifacial Spasm, Hereditary Spastic Paraplegia, Herpes Zoster Oticus, HIV/AIDS, HIV/AIDS Dementia Complex, Holmes-Adie Syndrome, Holoprosencephaly, Homocystinurua, Hughes Syndrome, Huntington's Disease, Hydramyelia, Hydranencephaly, Hydrocephalus, Hydromyelia, Hypersomnia, Hypertonia, Hypotonia Increased Intracranial Pressure, Infantile Hypotonia, Infantile Neuroaxonal Dystrophy, Infantile Refsum Disease, Infantile Spasms/West Syndrome, Iniencephaly, Intrauterine Teratogen Exposure, Isaac's Syndrome, Joubert Syndrome, Kawasaki Disease, Kearns-Sayre Syndrome, Kennedy's Disease, Kinsbourne Syndrome, Kleine-Levin Syndrome, Klinefelter Syndrome, Klippel-Feil Syndrome, Klippel-Trenaunay Syndrome, Kluver-Bucy Syndrome, Krabbe Disease, Kuru Lambert-Eaton Myasthenia Syndrome, Landau-Kleffner Syndrome, Lead Poisoning Leigh's Disease, Lennox-Gastaut Syndrome, Lesch-Nyhan Syndrome, Lewy-Body Dementia, Lipoid Proteinosis Lissencephaly, Locked-in Syndrome, Lyme Disease, Machado-Joseph Disease, Macrencephaly, Maple Syrup Urine Disease, Mathematics Disorders Meakes Disease, Meningitis, Microcephaly, Migraine, Mitochondrial cardiomyopathies, Mitochondrial Myopathies, Megalencephaly, Melkersson-Rosenthal Syndrome, Mental Retardation, Metachromatic Leukodystrophy, Miller-Fisher Syndromes, Mobius Syndrome, Monomelic Amyotrophy, Motor Neuron Diseases, Moyamoya Disease, Mucopolysaccharidosis, Multifocal Motor Neuropathy, Multi-Infarct Dementia. Multiple Sclerosis, Multi-System Atrophy with Orthostatic Hypotension, Multi-System Atrophy without Orthostatic Hypotension, Muscular Dystrophy, Myasthenia Gravis, Myoclonus Myopathy, Myotonia, congenital Narcolepsy, Neuroacanthocytosis, Neurofibromatosis. Neuroleptic Malignant Syndrome, Neuronal Ceroid Lipofuscinoses, Neurosarcoidosis, Neurosyphilis, Neurotoxicity, Niemann-Pick Disease, Nonverbal Learning Disability, Normal Pressure Hydrocephalus Occipital Neuralgia, Ohtahara Syndrome, Olivopontocerebellar Atrophy, Opsoclonus Myoclonus, Orthostatic Hypotension, Paraneolastic Syndromes, Parasthesias, Parkinson's Disease, Paroxysmal Choreoathetosis, Paroxysmal Hemicrania, Parry-Romberg, Pelizaeus-Merzbacher Disease, Periarteritis Nodosa, Peripheral Neuropathy, Periventricular Leukomalacia, Pick's Disease, Piriformis Syndrome, PKU Polymyositis Pompe Disease, Porencephaly, Postural Tachycardia, Prader Willi, Primary Lateral Sclerosis, Primary Progressive Aphasia, Progressive Multifocal Leukoencephalopathy, Progressive Supranuclear Palsy, Pseudotumor Cerebri, Psychotic Disorders, Rasmussen's Encephalitis, Reading Disorders, Repetitive Motor Disorders, Restless Leg Syndrome, Rett Syndrome, Reye's Syndrome, Rheumatoid Arthritis, Sandhoff Disease, Schilder's Disease, Schizencephaly, Sclerodoma, Semantic Dementia, Septo-Optic Dysplasia, Shaken Baby Syndrome, Shingles, Sjogren's Syndrome, Sleep Apnea, Somatoform and Conversion Disorders, Sotos Syndrome, Spina Bifida, Spinal Cord Injuries, Spinal Muscular Atrophy, Spinocerebellar degeneration, Stiff-Person Syndrome, Striatonigral Degeneration, Sturge-Weber Syndrome, Subcortical-Vascular Dementia, SUNCT Headaches, Sydenham Chorea, Syncope Syringo-myelia, Systemic Lupus, Tabes Dorsalis, Takayasu's Disease, Tardive Dyskinesia, Tarlov Cysts, Tay-Sachs Disease, Tethered Spinal Cord Syndrome, TIAs Thoracic Outlet Syndrome, Thyrotosic Myopathy, Todd's Paralysis, Tourette's Disorder, other Tic Disorders, Transverse Myelitis, Traumatic Brain Injury, Trigeminal Neuralgia, Tropical Spastic Paraparesis, Troyer Syndrome, Tuberous Sclerosis, Turner Syndrome, Vasculitis, von Economo's Disease, von Hippel-Lindau Disease, Wallenberg Syndrome, Wegener's granulonoatosis, Wernicke-Korsakoff Syndrome, Whiplash, Whipple's Disease, Williams Syndrome, Wilson's Disease, Wolman's Disease, and/or Zellweger Syndrome.

In yet other embodiments, the neurological disorder is Alzheimer's disease, multiple sclerosis (MS), amyotrophic lateral sclerosis (ALS), spinocerebellar ataxias, trinucleotide repeat disorder, dementia, multiple system atrophy, HIV-associated neurocognitive disorders (HAND), or polyneuropathy, hearing loss, ataxia, retinitis pigmentosa, and cataract (PHARC), Parkinson's disease, essential tremor, cerebellar tremor, dystonic tremor, orthostatic tremor, Parkinsonian tremor, rubral tremor, or psychogenic tremor.

In certain embodiments, the combination steps comprise generating a risk score, and wherein if the risk score of the first subject is similar to the risk score of the second subject, the first subject has a heightened risk of developing the neurological disorder.

In some other embodiments, the method further comprises developing and implementing a treatment plan to the first subject, the treatment plan comprising administering a therapeutically effective composition to the first subject.

In another aspect, the disclosure provides a system comprising a processor and a memory. The memory has a neurodiagnostic algorithm and a plurality of data sets, the data sets including, biomarker screening data, diagnostic imaging data, behavioral test data, exposure to environmental risk factors, subject health data, family medical history data. The processor of this system is capable of reading the data sets, executing the neurodiagnostic algorithm or algorithms, and deriving a risk profile therefrom.

In some embodiments, the system further comprises a display means for visualizing the risk profile. In certain embodiments, the system memory is at locations distant from the processor.

In another aspect, the disclosure provides data subscription service accessing the data sets of the system, wherein the neurodiagnostic algorithm predicts treatment outcomes from the risk profile. In one embodiment, the subject health data is obtained from an individual asymptomatic for neurological disorders.

In another aspect, the disclosure provides a relational database comprising a plurality of subject-independent neurodiagnostic data sets. These data sets comprise biomarker screening data, diagnostic imaging data, behavioral test data, environmental risk factor data, and the one or more subject-dependent neurodiagnostic data sets further including subject medical history and subject family medical histories.

In another aspect, the disclosure provides a data subscription service for accessing the relational database.

The present disclosure also provides a method of providing neuroanalytical services. The method comprises generating a patient profile for neurological risk, whereby generating further comprises analyzing subject-independent neuroanalytical data sets and subject-dependent neuroanalytical data sets; and delivering the patient risk profile to an end user.

In some embodiments, subject-independent neuroanalytical data sets include third-party data of neurological disease-relevant biomarkers, neural imaging data, environmental risk factors for neurological disorders. Subject-dependent neuroanalytical data sets include subject and family medical, environmental exposure, and behavioral data medical history data.

In certain embodiments, the patient risk profile comprises an aggregated risk of individual risk factors delineated or calculated from the subject-independent neuroanalytical data sets and subject-dependent neuroanalytical data sets.

In some embodiments, an algorithm is biased to value risk higher from the subject-dependent neuroanalytical data as compared to risk from subject-independent neuroanalytical data.

In some embodiments, the risk profile is delivered to an end user using SaaS, PaaS, or IaaS-based service models. In some embodiments, the delivery is real-time or near real-time. In certain embodiments, the end user obtains the risk profile on a tablet, smartphone or portable computing device.

In some embodiments, Private and Public Cloud architecture is employed.

BRIEF DESCRIPTION OF THE DRAWINGS

The foregoing and other objects of the present disclosure, the various features thereof, as well as the disclosure itself may be more fully understood from the following description, when read together with the accompanying drawings in which:

FIG. 1 is a diagrammatic representation of how the data can support a diagnosis of a neurological disorder, and select a useful population of subjects for a clinical trial for a therapeutic.

DESCRIPTION

The issued U.S. patents, allowed applications, published foreign applications, and references that are cited herein are hereby incorporated by reference in their entirety to the same extent as if each was specifically and individually indicated to be incorporated by reference. Patent and scientific literature referred to herein establishes knowledge that is available to those of skill in the art.

Unless otherwise defined, all technical and scientific terms used herein have the same meaning as commonly understood by one of ordinary skill in the art to which this disclosure belongs.

The present disclosure provides methods of predicting the risk of a subject for developing a certain neurological disorder using information derived from data sets obtained from a mammalian subject or groups of subjects. Such predictive methods are also useful for following the development of a neurological disorder or disease, and for selecting an appropriate subject pool for conducting a clinical trial on the therapeutic efficacy of a novel drug or diagnostic.

A. Sources of Data: How/What Data is Obtained

Information about a single subject or multiple subjects, are obtained from a data source or number of sources. These data sets are then related to the health and physical state of the subject.

For example, one such data source is the results obtained from screening assays for biomarkers, the presence or absence of which is indicative of the presence or predisposition for, a neurological disease or disorder. The biomarker can be any physically present substance, trait, or characteristic found in or on the subject. For example, the biomarker can be a nucleic acid, protein, polypeptide, peptide, prion, virus, brain plaque, CNS plaque, fibril, intranuclear neuronal inclusions, and/or brain structure abnormality.

Some useful biomarkers include a nucleic acid which is a gene or portion thereof, such as a coding portion, a single nucleotide polymorphism (SNP), an mRNA, microRNA (miRNA), a primary transcript of a miRNA (pri-miRNA), or a prepri-miRNA. For example, some useful nucleic acids include an over-expressed miRNA, such as miR-196a, miR-29a, or miR-330, or an under-expressed miRNA, such as miR-133b, miR-205, miR-34b/c, miR-9, miR-9*, or miR-132. Other useful nucleic acid biomarkers are mutant nucleic acids, such as a mutation in the Cu/Zn superoxide dismutase 1 (SOD1) gene, an unstable microsatellite repeat (insertion mutation) in a gene, HTT gene, androgen receptor on the X chromosome, ATXN1, ATXN2, ATXN3, ATXN7, TBP, CACNA1A, mutation in C9orf72 (on chromosome 9), FMR1 (on the X-chromosome), AFF2 (on the X-chromosome), FMR2 (on the X-chromosome), FXN or X25, (frataxin-reduced expression), DMPK, OSCA or SCA8, PPP2R2B or SCA12, α-synuclein, leucine-rich repeat kinase 2 (LRRK-2), glucocerebrosidase (GBA), ABHD12, SNCA, or LRRK2.

Other types of useful biomarkers include proteins, polypeptides, and peptides such as, but not limited to, a surface marker, tau protein, beta amyloid, polyglutamate (peptide), alpha-synuclein, non-Abeta component (NAC), polyQ expansion, TDP-43 protein aggregate, FUS protein aggregate, or a mutant Huntingtin aggregate. Peptides, polypeptides, and proteins can be detected using one of the many methods know to those with skill in the art (see, e.g., *Meth. Mol. Biol.* (2009) 536:588; Kurien et al. (eds.) Humana Press). The biomarker may also be a prion. Those with skill in the art are aware of methods of detecting prions (see, e.g., Atarashi et al. (2008) *Nat. Meth.* 3:2011-2012). The biomarker may be a Lewy body fibril, a neurofibrillary tangle, or an alpha-synuclein fibril amyloid plaque, or a senile plaque, found in the CNS in general or in the brain. Methods of detecting brain plaques are known to those with skill in the art (see, e.g., Kepe et al. (2006) *Meth. Enzymol.* 412:144-60), as are methods of detecting neurofibrillary tangles (see, e.g., Murphy et al. (1996) *Am. J. Pathol.* 149(6):1839-46).

The biomarker may also or alternatively be a virus such as, but not limited to Herpes simplex virus-1 (HSV-1 type HHV-1), roseolovirus (type HHV-6), Epstein Barr virus (EBV type HHV-4), Varicella zoster virus (VZV type HHV3), H1N1 Influenza viruses, HIV, or HTLV-I. Methods for detecting and characterizing virus and viral particles are well known to those with skill in the art (see, e.g., *Mol. Meth. Virus Detect.* (1995) (Wiedbrauk and Farkas, eds.) ISBN: 978-0-12-748920-9).

Certain physical characteristics of the subject provide another source of data. Such characteristics include age, body temp, heartbeat, pulse, sex, ethnicity, body weight, REM, electrical signals from the heart, body mass index (BMI), and height. Other physical characteristics include the constitution of body fluids, such as breath, blood, plasma, lymph, saliva, seminal fluid, urine, vaginal secretions, lacrimal secretions, mucous, sweat, and/or mammary secretions. Methods of analyzing the chemical makeup of body fluids is well known in the art (see, e.g., Frascione et al. (2012) *Analyst* 21; 137(2):508-12; Hu, et al. (2006) *Proteomics* 6(23): 6326-6353). Other physical factors which can be measured include the presence of certain genetic polymorphisms (Shi et al. (1999) *Mol. Diag.* 4(4):343-51), endocrine conditions (Cho et al. (2010) *J. Microbiol. Biotechnol.* 20(11):1563-70), oxidative stress ("Oxidative Stress and Nanotechnology, Methods and Protocols" *Meth. Mol. Biol.* (2013) 1028, (Armstrong et al., eds.) Humana Press), inflammation (Fischman et al. (1988) *Sem. Nucl. Med.* 18(4): 335-344), stroke (Kloska et al. (2004) *Neuroradiol.* 233 (1), traumatic brain injury (Vespa et al. (1999) *J. Neurosurg.* 91(5): 750-760), hypertension (Pickering (1994) *Lancet* 344(8914): 31-35), diabetes (C. M. Bennett, et al. (2007) *Diabetic Med.* 24 (4):333-343), head/CNS trauma (Orrison et al. (1994) *AJNR* 15:351-356), depression (Garland et al. (2002) *BCMJ.* 44(9): 469-472), infection (Ou et al. (1988) *Sci.* 239(4837): 295-297), cancer (Ferrari (2005) *Nature Rev.* (2005) 5:161-171), vitamin deficiency (Bates (1999) *Oxford J., Br. Med. Bull.* 55 (3): 643-657), and/or immune and/or metabolic conditions (Theofilopoulos et al. (1976) *J. Clin. Invest.* 57(1): 169-182; Oh et al. (2000) *Met. Eng.* 2:201-209). Other physical factors which can be measured include the presence of certain genetic polymorphisms, endocrine conditions, oxidative stress, inflammation, stroke, traumatic brain injury, hypertension, diabetes, head/CNS trauma, depression, infection, cancer, vitamin deficiency, and/or immune and/or metabolic conditions.

Another data source is related to information about various internal organs or systems within the subject. Such data is obtainable using various imaging methodologies. For example, depending on what type of information is being sought, the diagnostic imaging can be performed by taking an x-ray, a CAT scan, MRI, fMRI for BOLD imaging, SPECT perfusion image, CT scan, proton MR spectroscopy scan, PET scan, and/or 18F-FDG PET scan, and/or ultrasound. These scans can employ radio-labeled imaging reagents such as DaTScan, Amyvid, and similar reagents, which target specific receptors on neurons or proteins in the brain.

Yet another source of data is information obtained by performing behavioral tests indicative of the presence of, or predisposition for, various neurological disorders. Results of behavioral tests performed by the subject can be indicative of the predisposition, presence, or level of severity, of the neurological disorder. Such behavioral test can be any one known in the art, or later developed, which measures sensory abilities, such as acoustic startle, eye blink, pupil constriction, visual cliff, auditory threshold, and olfactory acuity. Useful behavioral tests also include those that measure motor functions, pain/pressure/temperature threshold(s), learning abilities, memory, and those which measure behavioral symptoms of anxiety, depression, schizophrenia, and/or drug addiction. Cognitive tests which assess the cognitive capabilities of humans and other animals, such as IQ tests, mirror tests (a test of visual self-awareness), and the T maze test (which tests learning ability) are useful as well. One with skill in the art is aware of many of such behavioral tests (see, e.g. (Benson (1993) *Neurol. Clin.* 11 (1): 1-8; Farah et al. (1996) *Behavioral Neurology and Neuropsychology* (McGraw-Hill Profess. Pub.) 1st ed.; Valenstein et al. (2003) *Clin. Neuropsychol.* (4th ed.) Oxford Univ. Press; Lione et al. (1999) *J. Neurosci.* 19(23):10428-10437).

Still another data source is from information about the subject's exposure to certain environmental factors. For example, the subject's exposure to pesticides, herbicides, fungicides, solvents, other toxic chemicals, tobacco or marijuana smoke, heavy metals, electromagnetic fields, ultraviolet radiation, and/or diet (malnutrition, vitamin deficiency), and/or alcohol consumption is measured. In particular examples, exposure to MPTP (1-methyl-4-phenyl-1,2,3,6-tetrahydro-pyridine), rotenone, paraquat, maneb, Agent Orange, manganese, lead, iron, methylmercury, mercury, copper, zinc, selenium, polychlorinated biphenyls, and/or a reactive oxygen species (ROS)(such as oxygen ions and peroxides) is measured. Methods for detecting exposure to various environmental toxins are known to those with skill in the art (see, e.g., *The Fourth National Report on Human Exposure to Environ. Chem.* (2009) CDCP; Wang et al. (2009) *Nano Lett.* 9(12): 4147-4152; Asphahani et al. (2007) *Analyst* 132(9): 835-841.) In some cases, exposure to the environmental factor measured causes apoptosis, oxidative stress, perturbed calcium homeostasis (loss of intracellular $Ca^{+2}$), excitotoxicity, mitochondrial dysfunction, and/or activation of caspases in the subject.

Another data source is the family history of the subject for the neurological and/or other disorders. Factors such as the prevalence of the disorder in the close versus extended family, at what age the disorder presented in these family members, the severity of the disorder, and its ability to be successfully treated in a close relative or extended family member are useful data.

The combination and manipulation of this data provides a wealth of information, such as the risk of developing a particular neurological disorder, the presence of the disorder in a yet asymptomatic (pre-symptomatic) subject, the level of severity of the disorder in a symptomatic subject, and what therapeutic measures should be taken to prevent or treat the pre-symptomatic or symptomatic subject.

For example, the data can be used in a method of predicting the risk of the development of a neurological disorder in a mammalian subject. The method comprises collecting data about the subject from a number of different sources, including: screening for the presence of a biomarker (indicative of the neurological disorder); performing diagnostic imaging of the subject; performing behavioral tests indicative of the neurological disorder; measuring the subject's exposure to an environmental factor; measuring/identifying a physical characteristic of the subject; and determining the family history of the subject for the neurological disorder, the combined data obtained from these activities being indicative of the presence of, or risk of developing, the disorder.

The data collected from the above-described sources can be organized by subject or pool of subjects, or by data source. In addition, this data can be obtained from a single time point or multiple time points.

For example, latitudinal data is data collected from one subject using different sources (i.e., different types of testing, as described in detail below) at one time point. Latitudinal data from the same source (I.e., same type of testing) can also be obtained from multiple subjects. Subjects are asymptomatic or symptomatic. Asymptomatic subjects are either control subjects who never develop the disorder, or are pre-symptomatic subjects who will develop the disorder at a later time.

Longitudinal data is data collected from the same subject using different sources obtained at different time points. For example, If the subject is asymptomatic when the first collection of data is obtained, this collection time point will be point 0 (longitudinal). Data will be collected at later time points from the same source(s). Data from multiple subjects obtained from a single source (same type of testing) can be tracked longitudinally as well.

B. Neurological Disorders

The neurological disorders to be tracked can be any disorder which affects the function of central nervous system (CNS) including the brain and/or spinal cord, of a mammalian subject. The mammalian subject can be any mammal, including a human, bovine, equine, canine, porcine, feline, murine, rattine, lepine, hircumine, cervine, ovine, etc. The subject can be asymptomatic or having symptoms of a neurological disorder.

For example, such a disorder can be a neurodegenerative disorder resulting from the degeneration of a component of the nervous system. The disorder may be a neurotrauma disorder resulting from a physical injury. In addition, the disorder may be a neuropsychology disorder which includes any disorder or injury resulting in an atypical psychological characteristic or behavior, and thus neuropsychology disorders may also be neurodegenerative and/or neurotrauma disorders. The disorder can have any etiology, including, but not limited to, a bacterial, fungal, viral, or prionic infection, a genetic mutation or polymorphism, traumatic injury, or exposure to any number of environmental toxins, irradiation, etc.

The neurodegenerative disorder can be a polyglutamine (PolyQ) disease, such as, but not limited to, pinocerebellar ataxia type 1 (SCA1), SCA2 (Spinocerebellar ataxia Type 2), SCA3 (Spinocerebellar ataxia Type 3 or Machado-Joseph disease), SCA6 (Spinocerebellar ataxia Type 6), SCA7 (Spinocerebellar ataxia Type 7), SCA17 (Spinocerebellar ataxia Type 17), DRPLA (Dentatorubropallidoluysian atrophy), HD (Huntington's disease), SBMA (Spinobulbar muscular atrophy or Kennedy disease), dentatorubral atrophy or pallidoluysian atrophy. Alternatively, the disorder can be a non-polyglutamine disease, such as, but not limited to, disease is FRAXA (Fragile X syndrome), FXTAS (Fragile X-associated tremor/ataxia syndrome), FRAXE (Fragile XE mental retardation), FRDA (Friedreich's ataxia), DM (Myotonic dystrophy), SCA8 (Spinocerebellar ataxia Type 8), or SCA12 (Spinocerebellar ataxia Type 12. The disorder may instead be Alzheimer's disease, multiple sclerosis (MS), amyotrophic lateral sclerosis (ALS), spinocerebellar ataxias, trinucleotide repeat disorder, dementia, multiple system atrophy, HIV-associated neurocognitive disorders (HAND), or polyneuropathy, hearing loss, ataxia, retinitis pigmentosa, and cataract (PHARC), Parkinson's disease, essential tremor, cerebellar tremor, dystonic tremor, orthostatic tremor, Parkinsonian tremor, rubral tremor, or psychogenic tremor.

The neuropsychology disorder may be Arachnoid cysts, Arachnoiditis, Asperger's Syndrome, Ataxia Telangiectasia, Arteriovenous Malformations, Attention Deficit/Hyperactivity Disorder, Autism Barth Syndrome, Batten Disease, Behcet's Disease, Bell's Palsy Bernhardt-Roth Syndrome, Binswanger's Disease, Blepharospasm Bloch-Sulzberger Syndrome, Brown-Sequard Syndrome, CADASIL Canavan Disease, Capgrass Syndrome, Causalgia Central Cord Syndrome, Central Pain Syndrome, Central Pontine Myelinosis, Cerebellar Hypoplasia, Cerebral Anoxia/Hypoxia, Cerebral Arteriosclerosis, Cerebral Cavernous Malformations, Cerebral Palsy, Cerebro-Oculo-Facio-Skeletal Syndrome, Charcot-Marie-Tooth Disease, Chiari Malformations, Childhood Anxiety Disorders, Childhood Disintegrative Disorder, Childhood Mood Disorders, Cholesteryl-Ester Storage Disease, Chronic Inflammatory Demyelinating Polyneuropathy, Chronic Pain Syndrome, Chung-Strauss Syndrome, Cluster Headaches Coffin-Lowry Syndrome, Colprocephaly Coma & Persisting Vegetative State Conduct Disorder, Oppositional Defiant Disorder, Congenital Myasthenia Congenital Myopathy, Corticobasal Degeneration, Craniosynostosis, Creutzfeld-Jakob Disease, Cushing's Disease, CVAs, Cytomegalovirus Dandy-Walker Syndrome, Dawson Disease, De Morsier's Syndrome, Dejerne-Klumpke Palsy Delirium, Dementia Pugilistica, Dermato-myositis, Devic's Disease, Diabetic Neuropathy, Disconnect Syndromes, Disorders of Written Language, Down Syndrome, Dravet Syndrome, Dysautonomia, Dyssynergia, Cerebellaris Myoclonica Dystonias, Empty Sella Syndrome, Encephalitis, Encephalopathy, Encephaloceles, Epilepsy, Erb-Duchenne Palsy, Fabry Disease, Fahr's Syndrome, Familial Periodic Paralyses, Familial Spastic Paraplegia, Farber's Disease, Fatal Familial Insomnia, Febrile Seizures, Fibromuscular Dysplasia, Fibromyalgia, Fragile X Syndrome, Friedeich's Ataxia, Frontotemporal Dementia, Gaucher Disease, Gerstmann-Straussler-Scheinker Disease, Gerstmann Syndrome, Glossopharyngeal neuralgia, Guillain-Barre, Hallervorden-Spatz Disease, Hemicrania, Continua Hemifacial Spasm, Hereditary Spastic Paraplegia, Herpes Zoster Oticus, HIV/AIDS, HIV/AIDS Dementia Complex, Holmes-Adie Syndrome, Holoprosencephaly, Homocystinurua, Hughes Syndrome, Huntington's Disease, Hydramyelia, Hydranencephaly, Hydrocephalus, Hydromyelia, Hypersomnia, Hypertonia, Hypotonia Increased Intracranial Pressure, Infantile Hypotonia, Infantile Neuroaxonal Dystrophy, Infantile Refsum Disease, Infantile Spasms/West Syndrome, Iniencephaly, Intrauterine Teratogen Exposure, Isaac's Syndrome, Joubert Syndrome, Kawasaki Disease, Kearns-Sayre Syndrome, Kennedy's Disease, Kinsbourne Syndrome, Kleine-Levin Syndrome, Klinefelter Syndrome, Klippel-Feil Syndrome, Klippel-Trenaunay Syndrome, Kluver-Bucy Syndrome, Krabbe Disease, Kuru Lambert-Eaton Myasthenia Syndrome, Landau-Kleffner Syndrome, Lead Poisoning Leigh's Disease, Lennox-Gastaut Syndrome, Lesch-Nyhan Syndrome, Lewy-Body Dementia, Lipoid Proteinosis Lissencephaly, Locked-in Syndrome, Lyme Disease, Machado-Joseph Disease, Macrencephaly, Maple Syrup Urine Disease, Mathematics Disorders Meakes Disease, Meningitis, Microcephaly, Migraine, Mitochondrial cardiomyopathies, Mitochondrial Myopathies, Megalencephaly, Melkersson-Rosenthal Syndrome, Mental Retardation, Metachromatic Leukodystrophy, Miller-Fisher Syndromes, Mobius Syndrome, Monomelic Amyotrophy, Motor Neuron Diseases, Moyamoya Disease, Mucopolysaccharidosis, Multifocal Motor Neuropathy, Multi-Infarct Dementia. Multiple Sclerosis, Multi-System Atrophy with Orthostatic Hypotension, Multi-System Atrophy without Orthostatic Hypotension, Muscular Dystrophy, Myasthenia Gravis, Myoclonus Myopathy, Myotonia, congenital Narcolepsy, Neuroacanthocytosis, Neurofibromatosis. Neuroleptic Malignant Syndrome, Neuronal Ceroid Lipofuscinoses, Neurosarcoidosis, Neurosyphilis, Neurotoxicity, Niemann-Pick Disease, Nonverbal Learning Disability, Normal Pressure Hydrocephalus Occipital Neuralgia, Ohtahara Syndrome, Olivopontocerebellar Atrophy, Opsoclonus Myoclonus, Orthostatic Hypotension, Paraneolastic Syndromes, Parasthesias, Parkinson's Disease, Paroxysmal Choreoathetosis, Paroxysmal Hemicrania, Parry-Romberg, Pelizaeus-Merzbacher Disease, Periarteritis Nodosa, Peripheral Neuropathy, Periventricular Leukomalacia, Pick's Disease, Piriformis Syndrome, PKU Polymyositis Pompe Disease, Porencephaly, Postural Tachycardia, Prader Willi, Primary Lateral Sclerosis, Primary Progressive Aphasia, Progressive Multifocal Leukoencephalopathy, Progressive Supranuclear Palsy, Pseudotumor Cerebri, Psychotic Disorders, Rasmussen's Encephalitis, Reading Disorders, Repetitive Motor Disorders, Restless Leg Syndrome, Rett Syndrome, Reye's Syndrome, Rheumatoid Arthritis, Sandhoff Disease, Schilder's Disease, Schizencephaly, Sclerodoma, Semantic Dementia, Septo-Optic Dysplasia, Shaken Baby Syndrome, Shingles, Sjogren's Syndrome, Sleep Apnea, Somatoform and Conversion Disorders, Sotos Syndrome, Spina Bifida, Spinal Cord Injuries, Spinal Muscular Atrophy, Spinocerebellar degeneration, Stiff-Person Syndrome, Striatonigral Degeneration, Sturge-Weber Syndrome, Subcortical-Vascular Dementia, SUNCT Headaches, Sydenham Chorea, Syncope Syringomyelia, Systemic Lupus, Tabes Dorsalis, Takayasu's Disease, Tardive Dyskinesia, Tarlov Cysts, Tay-Sachs Disease, Tethered Spinal Cord Syndrome, TIAs Thoracic Outlet Syndrome, Thyrotosic Myopathy, Todd's Paralysis, Tourette's Disorder, other Tic Disorders, Transverse Myelitis, Traumatic Brain Injury, Trigeminal Neuralgia, Tropical Spastic Paraparesis, Troyer Syndrome, Tuberous Sclerosis, Turner Syndrome, Vasculitis, von Economo's Disease, von Hippel-Lindau Disease, Wallenberg Syndrome, Wegener's granulonoatosis, Wernicke-Korsakoff Syndrome, Whiplash, Whipple's Disease, Williams Syndrome, Wilson's Disease, Wolman's Disease, and/or Zellweger Syndrome.

C. Relational Neurological Databases, Systems and Uses

The above information and data is included in a neurobiological analysis system. Such a system can further include, for example, a processor as well as memory, the memory used to store and retrieve data records while the processor applies instructions from an algorithm. Speed, scalability, memory and processing power, and communication bandwidth are significant to the efficient operation of the system. The system should be capable of managing and processing multiple large data files in parallel. Data sets include at least one or more data files, for example, biomarker screening data, diagnostic imaging data, behavioral test data, exposure to environmental risk factors, subject health data, and family medical history data. Thus the processor must be capable of reading the data sets, executing the algorithm and deriving the solution in the form of a subject data-specific file, i.e., the "risk profile" therefrom. Such systems that are known in the art and are suitable for use in accordance with the disclosure include those running Intel or Motorola processors, as well as larger supercomputer systems such as Cray XC30 and similar systems.

In one aspect, the system of the present disclosure includes a relational database. A relational database is provided with a plurality of data entries stored in the database. The data entries have a hierarchical relationship. The data entries are assigned an item identifier that uniquely identifies each of the data items. A multiple digit outline number is assigned to each of the data entries wherein the digits of the outline number correspond to the hierarchical levels of the data entries. A hierarchical level identifier is assigned to each of the data entries wherein the hierarchical level identifier equal the number of non-zero digits in the outline number. An organizational table is created wherein the table includes a row for each of the data entries and the table includes multiple columns. The columns comprise a column for the item identifier, a plurality of outline number columns where each outline number column comprises one digit of the outline number such that each of the digits is stored in a separate column, and a hierarchical level column comprising the level identifier.

Similarly, U.S. Pat. No. 8,280,750 provides examples of a useful patient data mining system and method. Herein, such a system and method for screening for neurological disease or injury is provided. The method includes the steps of retrieving a test for assessing risk of neurological disorder, the test including a plurality of data fields relating to neurological disease or injury risk factors; accessing a database to populate the data fields with information of an individual patient; and calculating a risk assessment of the individual patient developing neurological disease. A system includes a first database including a plurality of structured computerized patient records; a second database including a knowledge base relating to neurological disease, the second database including at least one test for determining neurological disease risk; and a processor for retrieving the at least one test from the second database, populating the at least one test with patient information retrieved from the first database and calculating a risk assessment for at least one patient. The method may further include retrieving first medical data associated with one patient from a database, identifying a probability that a medical device or drug or treatment regimen provides a medical benefit to the one patient that exceeds a cost associated with providing the medical device etc. to the one patient with reference to the first medical data and a probabilistic model, the probabilistic model having a plurality of model parameters, each model parameter corresponding to one type of datum in the first medical data, and providing the medical device etc. to the one patient in response to the identified probability exceeding a first predetermined threshold. See, for example, U.S. Publication No. 2013/0124224.

The present system built in accordance with the applications described herein is based on data mining and knowledge discovery technology. The system contains data mining models stored in the database. The models use the classification approach algorithms of data mining technology to measure and predict the survivability of patients based on the medical records of the patients. The models are designed to predict the percentage of survivability years after the time of diagnosis. The system contains novel user-friendly interfaces, which allow the user to register the medical variables of the patients so monitored, for example, to predict responses to treatments, suggest early intervention, and generate survivability and quality of life reports and predictions. The system also contains a set of functionality that allows the system administrators to control and monitor the contents of the database, and gate receipt of information, for example, in accordance with HIPAA and clinical requirements, or for subscription purposes. See, for example, U.S. Publication No. 2013/0173282.

In many countries, health and patient privacy laws require de-identification of certain medical records. This is accomplished by means known in the art. For example, WO 2006015100 describes a method for linking de-identified patients using encrypted and unencrypted demographic and healthcare information from multiple data sources. As applied herein, the present system includes a longitudinal database of de-identified patient healthcare transaction data records linked by longitudinal linking tags (IDs). A new healthcare transaction data record, which may include alphanumeric identification code attributes, third party attributes and/or demographic attributes, is assigned an linking ID associated with a previous healthcare transaction data record based upon successful comparison of either a designated set of identification code attributes or a designated set of demographic attributes. The longitudinal data base is assembled by a matching process in which a new data record is compared level by level with previous healthcare transaction data records through a hierarchy of a first series of matching levels each defined by a designated set of alphanumeric identification code attributes and a second series of matching levels each defined by a designated set of attributes including demographic attributes and then assigned the ID associated with a successfully matched reference data record.

The system is useful for identifying groups of patients with similar physiological characteristics and risk profiles. The present system also provides for partitioning a plurality of patients into risk profile groups. See, for example, U.S. Publication No. 2010/0016743. Such a system is useful for determining patient treatment response outcomes. See, for example, U.S. Pat. No. 8,655,817.

A medical digital expert system is provided, to predict a patient's response to a variety of treatments (using pretreatment information). The system utilizes data fusion, advanced signal/information processing and machine learning/inference methodologies and technologies to integrate and explore diverse sets of attributes, parameters and information that are available to select the optimal treatment choice for an individual or for a subset of individuals suffering from any illness or disease including psychiatric, mental or neurological disorders and illnesses. The methodology and system can also be used to determine or confirm medical diagnosis, estimate the level, index, severity or critical medical parameters of the illness or condition, or provide a list of likely diagnoses for an individual suffering/experiencing any illness, disorder or condition.

The systems and methods of the present application includes embodiments that allow users to more easily and efficiently compare medical data in an automated, computerized system using a variety of visualization tools, by operation on datasets sourced from a variety of entities. See, for example, U.S. Publication No. 2014/0022255.

The system is adaptable for integration into physician work systems. For example, electronic patient records and documentation are usable with push and pull of the data to and from the database. See, for example, U.S. Pat. No. 8,566,123. Medical records software interfaces in the system, allow a clinician, e.g., nurse or doctor, to combine entry of new patient orders, prescriptions, flowsheet observations, etc. in their workflow to interface and pull patient data from a database into their display. The user can select on their user interface one or more categories of a patient record, e.g., significant events, scans, tests or orders, and view or edit prior entries in the database in these categories, and add additional documentation. The documentation is written or pushed to defined areas of the database, one devoted to patient documentation and a second area corresponding to the selected category, e.g., orders. The method and apparatus improves workflow efficiency and promotes a smooth transition from the thought process of the clinician to the ordering or prescription process, without the need for changing venues or screen displays.

The system of the present disclosure may be executed and or delivered in whole or in part, via networks. For example, an Internet system for connecting healthcare providers and patients is described in U.S. Publication No. 2012/0284045. Networked systems provide for remote-based monitoring and patient feedback systems, which are incorporated into the database. See, for example, U.S. Publication No. 2014/0052464, which details a method and system for remote patient monitoring. A system for remotely monitoring a patient includes a plurality of input sources operable to acquire information corresponding to a well-being condition of a patient, an external database for storing analytical models and medical data, and a central control system being operable to receive the signals from the input sources, and execute an algorithm to select an analytical model from the database based on the (real-time) information and the data, analyze the information and the data with the parameters of a medical model to determine a state of the patient and formulate a health prediction, determine a recommendation as a result of the state and the health prediction, and transmit the recommendation to at least one external entity for providing support and assistance to the patient or to a caregiver of the patient.

An Internet-based system involves a database and search capabilities for connecting patients with healthcare providers, e.g., physicians, hospitals, nursing homes, treatment facilities, etc., clinical sites, etc., and further enables such providers to reach patients with whom they may not otherwise come into contact. A patient may access the healthcare provider information through a search conducted using a search engine, such as Google, Yahoo, etc. Alternatively, a patient may access the company Web site's predetermined Web page that provides search capabilities on its database. A patient may research a healthcare provider based on criteria specified by the patient. Information provided to the patient may be in the form of a report, profile, ratings, etc., including patient-provided information, physician-verified information, and information verified by an independent third party. The verified information and ratings provided by the Web site enable patients to differentiate among healthcare providers and thereby select the provider that best meets their individual needs.

Such systems of the present disclosure may further include integrated electronic patient health care and billing coordination systems, see, for example, U.S. Pat. No. 8,615,413. A patient care coordination system can include a plurality of hand-held computers in communication with a cloud computing network or a remote server that has an accessible database of all patients and the health care information of each. The cloud computing network or remote server synchronizes, in real time, patient health care information input in any one of the plurality of hand-held computers with all the others of the plurality of hand-held computers. The hand-held computers are able to download and view the patient health care information in the database in a user-friendly graphic user interface equipped with a touch screen for ease of user data navigation. The cloud computing network or remote server also receives, as input, data from patient care devices that are used to monitor patient condition periodically or continuously and store these in the database for the appropriate patient. In addition, the cloud computing network or remote server transmits encrypted electronic digital patient health care information to a third party and receives acknowledgment of third party receipt of the information. The cloud computing network or remote server monitors fee-bearing information exchanged with the third party and automatically assesses a predetermined fee based on fee-bearing information exchanged and stores the billing information to the appropriate patient in the data base.

D. Application of Systems to Clinical Trials

In yet another aspect, the disclosure provides a system and method that identifies patients for clinical drug or device trials. See, for example, U.S. Publication No. 2007/0106531. Such a system rapidly and precisely identifies patient candidates for clinical trials. It includes a database component operative to maintain a hospital patient database component and its plurality of hospital databases and their corresponding plurality of patient names and medical records, in communication with one or more medical practice database components and their corresponding plurality of specialties and their corresponding plurality of patient names and medical records. The method and system also include a clinical studies database component and its corresponding plurality of clinical studies, a communications component to receive changes to said database component, and a processor programmed to periodically match compatible patients and clinical studies, and to generate reports to medical practices in said medical practice database having matched patients. The processor may be programmed to search free text keywords and phrases.

In another aspect, the system analyzes patients with respect to clinical medical trials, see, for further example, U.S. Pat. No. 7,401,028. A system of the present disclosure provides for various methods for evaluating one or more patients for their potential in a medical study, and includes: a database component operative to maintain a medical practice database component and a clinical studies database component. The system further includes a component to observe changes to the database components, and a communications component to provide an alert, for example, to the patient, or a medical practitioner. The system also includes a processor programmed to update the database components, periodically match compatible medical specialties with the medical studies, and generate reports of the matched medical practices in the medical practice database.

The system may also include a fee database component, which the processor uses to calculate a fee for conducting the study.

E. Algorithms

The processor reads the data sets exemplified above, executing an algorithm and deriving the solution in the form of a subject data-specific file for display, or executing an outcome as desired. The particular algorithm employed may vary across particular applications. However, the objective in most instances where data is manipulated, one desirable outcome is generation of a risk-score or similarly predictive model based on the aggregation and weighting of data from relevant data sets, using common statistical tools and models. For example, detection of gene polymorphisms can be predictive of risk for disease, such as with Apolipoprotein E (ApoE) a polymorphic apolipoprotein, with three major isoforms: ApoE2, ApoE3 and ApoE4. ApoE4 is found in approximately 14 percent of the population, and has been implicated in atherosclerosis, Alzheimer's disease, impaired cognitive function, reduced hippocampal volume, faster disease progression in multiple sclerosis, unfavorable outcome after traumatic brain injury, ischemic cerebrovascular disease, sleep apnea, and reduced neurite outgrowth. Subjects that are homozygous for ApoE4 have a different risk profile than heterozygous subjects. However, high-quality, high-relevancy subject specific data is useful if it reflects an integration of various risk profiles for different types of data, when such data and risk is examined and evaluated in the aggregate. For example, the detection of ApoE4 in a subject with traumatic brain injury is informative, but imaging of the injury site and the healing process (e.g., longitudinal monitoring) provides a more refined analysis of the medical condition, and better prognosis. Similarly, multiple biomarker studies such as those from Genome Wide Association Studies (GWAS) provide more information than single biomarker tests. See, for example, Mailer et al., *Nature Genet.* (2006) 38:1055-1059, which shows that common variation in three genes, including a noncoding variant in CFH, strongly influences risk of age-related macular degeneration. Additional useful information will be apparent to medical professionals, and such data are considered in the aggregate to determine an outcome's probability and the possible best courses of treatment or prevention given statistics that are highly patient-relevant.

The algorithms useful herein are based on computational biology, bioinformatics and mathematical biology, which draw from mathematics and information science. They employ application of data-analytical and theoretical methods, mathematical modeling and computational simulation techniques to the study of biological and behavioral neuroscience. Their objective is application of computational tools and approaches for expanding the use of biological, medical, behavioral or health data, including those to acquire, store, organize, archive, analyze, or visualize such data. The derivation of an algorithm to parse individual data sets and quantitate an aggregate a value for their application, and the translation of such to machine-readable format is considered to be within the means of one of ordinary skill in the various arts, in view of such arts and the teachings provided herein.

Computational neuroscience is a rapidly evolving field, and is focused on the study of brain function in terms of the information processing properties of the structures that make up the nervous system. It models the brain in order to examine specific aspects of the CNS. Various types of models of the brain exist (see, e.g., Sejnowski, et al. (1988) *Computa. Neurosci.* 4871:241). These include realistic brain models and simplifying brain models. Realistic models look to represent every aspect of the brain, including as much detail at the cellular level as possible. Realistic models provide the most information about the brain, but also have the largest margin for error. Variables in a brain model create the possibility for additional error, and the models are further limited by knowledge of cellular structures. Realistic brain models are computationally intensive. Simplifying brain models look to limit the scope of a model in order to assess a specific physical property of the neurological system. This allows for less intensive computational resources for problems to be solved. The disclosure provides for improved algorithms and data structures relative to the ones currently used to increase the speed in calculating solutions to particular queries.

Likewise, computational pharmacology is essential for analyzing drug data, employing computational methods to analyze massive data sets. This allows for better evaluation of data and provides for more accurate clinical development of drugs. The models and algorithms of computational pharmacology are useful in applications whereby clinical and experimental studies are considered or undertaken. Particular and non-limiting examples include deriving exclusion criteria for a clinical study, and in real-time matching the suitability of a particular subject for a clinical study based on genetic and other biomarker information, scans, personal and family medical history.

Computational biomodeling is a field concerned with building computer models of complex biological systems. Computational biomodeling aims to develop and use visual simulations in order to assess the complexity of biological systems. This is accomplished through the use of specialized algorithms, and visualization software. These models allow for prediction of how systems will react under different environments. Computational biomodeling is of particular relevance to neuroscience, as the brain and nervous system are good examples of complex systems. Particular and non-limiting examples may include olfactory function test data as a predictor of Parkinson's risk, whereby modeling of olfactory function and function of dopamine-generating cells in the substantia nigra, a region of the midbrain, are monitored in parallel, over a time interval (e.g., a five-year longitudinal study).

F. Connectivity and Communications

In many embodiments, it is desirable that the above-described system be modular, but capable of rapid, or even real-time information exchange. A useful and non-limiting example is a system that stores data at multiple sites across a network (e.g., patient data at a physician's office; medical images and test results at a hospital and/or outpatient center; genetic frequencies and correlations at various Internet-accessible sites) and where the algorithm runs on a connected server or servers, rather than on a local computing device such as a desktop, laptop, PDA, tablet or smartphone. This is often described as "in the cloud," where a computing hardware machine or group of computing hardware machines commonly referred as a server or servers is connected through a communication network such as the Internet, an intranet, a local area network (LAN) or wide area network (WAN). Connectivity of various modules in and to the system will depend of the device. These are exemplified by: optical networks, ITU-T G.hn (1 Gigabit/s) local area networks or IEEE 802.11 (WiFi) networks.

Any individual user who has permission to access the server can use the server's processing power to run an application, store data, or perform any other computing task. Infrastructure as a service (IaaS), Platform as a service (PaaS) and Software as a service (SaaS) models are all applicable to the systems described herein.

G. Provision of Neuroanalytical Services

In accordance with the above system, data and methods, by way of further extrapolation and example, any individual user who has permission to access the system server can use the server's processing power to run an application, store/retrieve data, or perform any other computing task linking a plurality of datasets (e.g., subject-independent neuroanalytical data sets and subject-dependent neuroanalytical data sets). Users may receive or send content and data from smartphones, tablets, laptops, or dedicated devices (e.g., monitors). Delivery of information is real-time, or with minimal delays due to networks and processing delays. Infrastructure as a service (IaaS), Platform as a service (PaaS) and Software as a service (SaaS) models are all applicable to the systems described herein. In certain currently useful embodiments, two combinations and even all three models operate simultaneously.

SaaS delivers business processes and applications, as standardized capabilities for a usage-based cost at an agreed, business-relevant service level. All infrastructure and IT operational functions are abstracted away from the consumer. SaaS models are useful, for example, in applications that are used in the clinic.

PaaS delivers application execution services, for applications written for a pre-specified development framework. Service levels and operational risks are shared because the consumer must take responsibility for the stability, architectural compliance, and overall operations of the application while the provider delivers the platform capability (including the infrastructure and operational functions) at a predictable service level and cost. PaaS models are useful, for example, in applications that involve hospitals or imaging centers.

IaaS abstracts hardware into a pool of computing, storage, and connectivity capabilities that are delivered as services for a usage-based (metered) cost. Its goal is to provide a flexible, standard, and virtualized operating environment that can become a foundation for PaaS and SaaS. IaaS is usually seen to provide a standardized virtual server. The consumer takes responsibility for configuration and operations of the guest Operating System (OS), software, and Database (DB). Compute capabilities (such as performance, bandwidth, and storage access) are also standardized. Service levels cover the performance and availability of the virtualized infrastructure. The consumer takes on the operational risk that exists above the infrastructure. IaaS models are useful, for example, in applications that involve clinical trials.

In addition, various configurations are applicable. Public Cloud is a pool of computing services delivered over the Internet, with variations being Shared Public Cloud and Dedicated Public Cloud. The Dedicated Public Cloud provides functionality similar to a Shared Public Cloud except that it is delivered on a dedicated physical infrastructure. Private Cloud is a pool of computing resources delivered as a standardized set of services that are specified, architected, and controlled by a particular enterprise, driven by the need to maintain control of the service delivery environment because of application maturity, performance requirements, industry or government regulatory controls, or business differentiation reasons. Private Cloud may be Self-hosted Private Cloud, Hosted Private Cloud or Private Cloud Appliance. The particular classifications used to describe the disclosure will depend on the relationship between modules of the system used for particular information. For example, where the system is designed to access public data and compare subject information thereto, as to public biomarker data (such as Genbank) the disclosure will have Public Cloud features; and for certain aspects of subject data (such as subject genetic information/SNPs) the disclosure will have Private Cloud features. The architecture of the system will be apparent to one of skill in the information technology arts, in view of the teachings herein.

EQUIVALENTS

Those skilled in the art will recognize, or be able to ascertain, using no more than routine experimentation, numerous equivalents to the specific composition and procedures described herein. In particular, the above examples provide certain embodiments of the disclosure and are not intended to be limiting. The modular structure of the system and use of the data sets in various combinations for achieving different outcomes are considered to be within the means of one of ordinary skill in the various arts, in view of such arts and the teachings provided herein. Such equivalents are considered to be within the scope of this disclosure, and are covered by the following claims.

The invention claimed is:

1. A method of predicting the risk of developing a specific neurological disorder in a first mammalian subject asymptomatic for the specific neurological disorder, the method comprising the steps of:
    screening for the presence of one or more biomarkers, wherein the biomarker is not a nucleic acid;
    performing diagnostic imaging of the first subject;
    performing behavioral tests indicative of the predisposition for the specific neurological disorder;
    measuring the first subject's exposure to an environmental factor;
    measuring/identifying a physical characteristic of the first subject;
    determining the presence of the specific neurological disorder in a family member of the first subject; and
    combining results from the steps above, the combined results being obtained at a single time point and are latitudinal data from the first subject,
    comparing the combined latitudinal data of the first subject with combined latitudinal data obtained at a single time point from a second mammalian subject diagnosed with the specific neurological disorder, a high correlation between the combined latitudinal data from the second subject and the combined latitudinal data obtained from the first subject being indicative of a heightened risk of the first subject developing the specific neurological disorder.

2. The method of claim 1, wherein the screening step comprises screening for a biomarker which is a polypeptide, prion, virus, brain plaque, CNS plaque, fibril, intranuclear neuronal inclusions, and/or brain structure abnormality.

3. The method of claim 2, wherein the polypeptide is a surface marker, tau protein, beta amyloid, polyglutamate (peptide), alpha-synuclein, non-Abeta component (NAC), polyQ expansion, TDP-43 protein aggregate, FUS protein aggregate, or mutant Huntingtin aggregate.

4. The method of claim 2, wherein the biomarker is a Lewy body fibril, neurofibrillary tangle, or alpha-synuclein fibril.

5. The method of claim 2, wherein the biomarker is an amyloid plaque or a senile plaque.

6. The method of claim 2, wherein the biomarker is Herpes simplex virus-1 (HSV-1 type HHV-1), roseolovirus (type HHV-6), Epstein Barr virus (EBV type HHV-4), Varicella zoster virus (VZV type HHV3), H1N1 Influenza a viruses, HIV, and/or HTLV-II.

7. The method of claim 1, wherein the screening step is performed by obtaining a sample of a body fluid or tissue and screening for the biomarker in the sample.

8. The method of claim 7, wherein the body fluid is blood, cerebral spinal fluid, serum, lymph, saliva, lacrimal secretion, sweat, mucous, vaginal secretion, urine, or seminal fluid.

9. The method of claim 1, wherein the diagnostic imaging performed is an x-ray, a computerized axial tomographic (CAT) scan, magnetic resonance imaging (MRI) scan, functional MM (fMRI), single photon emission computed tomography (SPECT) perfusion image, computed tomography (CT) scan, proton MR spectroscopy scan, positron emission tomographic (PET) scan, and/or [F-18] fluoro-2-deoxy-D-glucose-positron emission tomographic (18F-FDG PET) scan, DatScan, and/or ultrasound.

10. The method of claim 1, wherein the behavioral test performed measures sensory abilities, motor functions, body weight, body temperature, and/or pain threshold, learning abilities, memory, and symptoms of anxiety, depression, schizophrenia, and/or drug addiction.

11. The method of claim 10, wherein the behavioral test performed measures acoustic startle, eye blink, pupil constriction, visual cliff, auditory threshold, and/or olfactory acuity.

12. The method of claim 1, wherein the first subject's exposure to pesticides, herbicides, fungicides, solvents, other toxic chemicals, tobacco smoke, heavy metals, electromagnetic fields, ultraviolet radiation, and/or diet (malnutrition, vitamin deficiency), and/or alcohol consumption is measured.

13. The method of claim 12, wherein the first subject's exposure to iMPTP (1-methyl-4-phenyl-1,2,3,6-tetrahydropyridine), rotenone, paraquat, maneb, Agent orange, manganese, lead, iron, methylmercury, copper, zinc, selenium, polychlorinated biphenyls, and/or a reactive oxygen species (ROS) is measured.

14. The method of claim 1, wherein the physical factor measured is age, gender, ethnicity, heart rate, REM, cardioelectrical signals, and/or the presence of genetic polymorphisms, endocrine conditions, oxidative stress, inflammation, stroke, traumatic brain injury, hypertension, diabetes, head/CNS trauma, depression, infection, cancer, vitamin deficiency, and/or immune and/or metabolic conditions.

15. The method of claim 1, wherein the neurological disorder is a neurodegenerative disorder, a neurotrauma disorder, and/or a neuropsychological disorder.

* * * * *